United States Patent
Olesen et al.

(10) Patent No.: US 7,851,492 B2
(45) Date of Patent: Dec. 14, 2010

(54) ERG CHANNEL OPENERS FOR THE TREATMENT OF CARDIAC ARRHYTHMIAS

(75) Inventors: Søren Peter Olesen, Klampenborg (DK); Morten Grunnet, København Ø (DK); Palle Christophersen, Ballerup (DK); Dorte Strøbæk, Farum (DK); Joachim Demnitz, København (DK); Rie S. Hansen, København S (DK)

(73) Assignee: Neurosearch A/S, Ballerup (DK)

( * ) Notice: Subject to any disclaimer, the term of this patent is extended or adjusted under 35 U.S.C. 154(b) by 1291 days.

(21) Appl. No.: 10/570,250

(22) PCT Filed: Sep. 6, 2004

(86) PCT No.: PCT/EP2004/052046

§ 371 (c)(1),
(2), (4) Date: Mar. 2, 2006

(87) PCT Pub. No.: WO2005/023237

PCT Pub. Date: Mar. 17, 2005

(65) Prior Publication Data

US 2006/0281794 A1    Dec. 14, 2006

(30) Foreign Application Priority Data

Sep. 4, 2003    (DK) ................................ 2003 01264

(51) Int. Cl.
*A61K 31/4245* (2006.01)
*A61K 31/4196* (2006.01)
*A61K 31/41* (2006.01)
*A61K 31/17* (2006.01)

(52) U.S. Cl. .................... 514/364; 514/381; 514/384; 514/563; 514/597

(58) Field of Classification Search .................... None
See application file for complete search history.

(56) References Cited

U.S. PATENT DOCUMENTS

| | | | | | |
|---|---|---|---|---|---|
| 5,104,890 | A | * | 4/1992 | Shiokawa et al. | 514/370 |
| 5,164,509 | A | * | 11/1992 | Atwal | 548/126 |
| 5,270,308 | A | * | 12/1993 | Shiraishi et al. | 514/229.8 |
| 5,416,097 | A | * | 5/1995 | Erhardt et al. | 514/320 |
| 5,679,706 | A | * | 10/1997 | D'Alonzo et al. | 514/456 |
| 5,696,138 | A | * | 12/1997 | Olesen et al. | 514/349 |
| 5,972,894 | A | * | 10/1999 | Sinackevich et al. | 514/16 |
| 6,353,016 | B1 | * | 3/2002 | Tanaka et al. | 514/422 |
| 2009/0047703 | A1 | * | 2/2009 | Trudeau | 435/29 |

FOREIGN PATENT DOCUMENTS

| | | |
|---|---|---|
| WO | WO-94/22807 A | 10/1994 |
| WO | WO-96/25157 A | 8/1996 |
| WO | WO-96/28537 A1 | 9/1996 |
| WO | WO-97/45111 A1 | 12/1997 |
| WO | WO-97/45400 A1 | 12/1997 |
| WO | WO-98/47879 A | 10/1998 |
| WO | WO-00/06772 A1 | 2/2000 |
| WO | WO-00/24707 A | 5/2000 |
| WO | WO-02/42417 A2 | 5/2002 |
| WO | WO-02/42735 A | 5/2002 |
| WO | WO-02/064128 A | 8/2002 |
| WO | WO-03/000245 A1 | 1/2003 |
| WO | WO-2004/022529 A | 3/2004 |
| WO | WO 2005023238 A1 * | 3/2005 |
| WO | WO-2007/062028 A2 | 5/2007 |

OTHER PUBLICATIONS

Clin.Cardiol., 27, 495-500, 2004; "Arrhythmias", www.americanheart.org., 2009.*

* cited by examiner

*Primary Examiner*—Brian-Yong S Kwon
(74) *Attorney, Agent, or Firm*—Birch, Stewart, Kolasch & Birch, LLP

(57) ABSTRACT

This invention relates to the use of ERG channel openers for the treatment of cardiac arrhythmias, and to the use of specific compounds for such treatment. In a separate aspect the invention provides novel compounds useful as ERG channel openers.

6 Claims, 4 Drawing Sheets

Control

Compound C

ERG CHANNEL OPENERS FOR THE TREATMENT OF CARDIAC ARRHYTHMIAS

TECHNICAL FIELD

This invention relates to the use of ERG channel openers for the treatment of cardiac arrhythmias, and to the use of specific compounds for such treatment. In a separate aspect the invention provides novel compounds useful as ERG channel openers.

BACKGROUND ART

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment or electrolyte imbalances. Such disturbances in the impulse are called arrhythmia or dysrythmia and they may lead to unease, emboli, syncope or sudden death.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore good targets for anti-arrhythmic cardiac drugs, and many anti-arrhythmic drugs on the market do exert their effect by interacting with ion channels.

One of the ion channels responsible for the termination of the cardiac action potential is the human ERG1 channel (Human Ether-a-go-go Related Gene channel, HERG1 channel), which is selective for permeation of potassium ions. Block of this channel caused by drugs or genetic dysfunction may lead to arrhythmia.

A number of drugs have been shown to block the ERG channels, including compounds as diverse as anti-psychotics, anti-depressants, anti-histamines and anti-biotics. Several of these drugs have been withdrawn from the market, or put on prescription, within recent years due to pro-arrhythmic effects. Pharmacological block of HERG1 channels leads to a prolongation of the cardiac action potential and a reduced potassium conductance during the repolarisation and resting phase of the action potential. The prolonged action potential is reflected in the ECG as an increased distance between the Q and T waves, and the condition is called acquired Long QT Syndrome. Patients being treated with HERG1 blocking drugs can develop serious ventricular tachy-arrhythmia called torsade-des-pointes, which may eventually lead to syncope and possibly cardiac arrest.

HERG1 channels are targets for a number of genetic mutations giving rise to inherited Long QT Syndrome. These patients also develop serious arrhythmias of the torsade-des-pointes type as well as a number of other arrhythmias including brady-arrhythmias. The patients are currently often treated with adrenergic beta-receptor blockers or pacemakers possibly with intracardial defibrillators (ICD).

Most of the existing anti-arrhythmic drugs on the market were developed before their molecular target was known. However, for many of them their molecular target has later been shown to be an ion channel.

Anti-arrhythmic drugs are usually divided into four main classes.

Class 1 compounds all block the cardiac voltage-dependent sodium channel. Some class 1 compounds do have additional effects influencing the cardiac action potential being the basis for a further subdivision into three subclasses:

Class 1A compounds are sodium channel blockers such as Quinidine or Disopyramid, which prolong the action potential.

Class 1B compounds are sodium channel blockers such as Lidocaine, Mexiletin or Phenytoin, which shorten the action potential.

Class 1C compounds are sodium channel blockers such as Flecainid or Propafenon, which do not change the action potential duration.

Class 1 compounds interact with the sodium channel during its open or inactivated state and are dissociated from the channels during its closed state (during diastole). The rate of dissociation determines whether they show a frequency-dependent channel block. Some of the class 1 compounds also block subtypes of potassium or calcium permeable channels in addition to their sodium channel blocking effect.

Class 2 compounds are β-adrenoceptor blockers and include drugs like Atenolol, Metoprolol, Timolol or Propranolol. β-adrenoceptor blockers can be selective for cardiac β1-receptors or have affinity for β1- as well as β2-receptors. Some of the compounds have an intrinsic β-stimulating effect too.

Class 3 compounds are potassium channel blockers such as Amiodaron, which prolong the action potential by delaying repolarisation of the action potential through block of potassium channels. Class 3 compounds show lack of effects in many patients and may even be pro-arrhythmic, probably due to the destabilising effect of the reduced potassium current.

Class 4 compounds are blockers of L-type calcium channels such as Verapamil.

In addition to the compounds allocated to those four classes, Digoxin and Adenosin also find use in the treatment of arrhythmia.

WO 96/28537 describes long QT genes and methods for diagnosing or preventing the occurrence of Long QT Syndrome. WO 00/06772 describes mutations in and genomic structure of HERG1, a Long QT Syndrome gene. WO 02/42417 describes a new human ERG (HERG2) channel. WO 02/42735 describes a method of identifying HERG channel inhibitors. However, the use of HERG1 channel openers for the treatment of cardiac arrhythmias has never been suggested.

Moreover, WO 94/22807, WO 96/25157, WO 97/45400, WO 97/45111, WO 98/47879, WO 00/24707 and WO 2004/022529 describe urea derivatives useful as potassium channel modulators or chloride channel blockers, but an effect on HERG1 channels have not been reported with these compounds.

SUMMARY OF THE INVENTION

The present invention is based on the discovery that whereas dysfunction or block of human ERG channels destabilises the cardiac myocytes and delays the repolarisation we have found that an increased cardiac ERG current helps repolarise the cardiac myocytes, and stabilises the cells during the repolarising and resting phase. The increased ERG current will inhibit early and late after-depolarisations as well as on the re-entry arrhythmia mechanism. ERG channel activation therefore is found useful for the treatment of all major cardiac arrhythmias.

As described above the HERG channel openers for use according to the present invention are different from known antiarrhythmic drugs and represent a new therapeutic principle, having the advantage of both increasing the potassium currents in the vulnerable period of the action potential, and of stabilising the cardiomyocytes following this period due to slow channel closure.

Next, the present invention is based on the discovery that certain urea and benzamide derivatives are useful as ERG channel activators.

Therefore, in its first aspect, the invention provides pharmaceutical compositions for the treatment, prevention or alleviation of a cardiac disease, disorder or condition in a mammal, including a human, which composition comprises
 a therapeutically effective amount of a compound capable of activating an ERG channel, and
 a pharmaceutically acceptable carrier or excipient.

In another aspect the invention relates to the use of a compound capable of activating an ERG channel, or a pharmaceutically-acceptable addition salt thereof, for the manufacture of a pharmaceutical composition/medicament for the treatment, prevention or alleviation of a cardiac disease, disorder or condition a mammal, including a human.

In still another aspect the invention provides a method of treatment, prevention or alleviation of a cardiac disease, disorder or condition of a living animal body, including a human, which disorder, disease or condition is responsive to activation of an ERG channel, which method comprises the step of administering to such a living animal body in need thereof, a therapeutically effective amount a compound capable of activating an ERG channel, or a pharmaceutically-acceptable addition salt thereof.

In a final aspect the invention provides novel compounds useful as ERG channel activators.

Other objects of the invention will be apparent to the person skilled in the art from the following detailed description and examples.

DETAILED DISCLOSURE OF THE INVENTION

ERG Channel Opening Compounds

Viewed from one aspect the present invention relates to the use of an ERG channel opening compound for the treatment, prevention or alleviation of a cardiac disease, disorder or condition in a mammal, including a human.

In the context of this invention an ERG channel opening compound is a compound that is capable of activating (reinforcing) an ERG current—at a concentration at or above 30 µmol, preferably at or above 10 µmol, more preferred at or above 1 µmol, most preferred at or above 0.1 µmol—as detected by electrophysiological methods, in particular by patch clamp technology, e.g. as described by Hamill O P, Marty A, Neher E, Sakmann B & Sigworth F J: Improved patch-clamp techniques for high resolution current recordings from cells and cell-free membrane patches; *Pflügers Arch.* 1981 391 85-100.

In a preferred embodiment the ERG channel opening compound of the invention preferably is a selective ERG channel opening compound.

In a preferred embodiment the ERG channel is an ERG1 channel. In a more preferred embodiment the ERG channel is a human ERG1 (Human Ether-a-go-go Related Gene channel, HERG1 channel) channel as the one cloned by Warmke & Ganetzky; *Proc. Natl. Acad. Sci. USA* 1994 91 3438-3442 and described functionally by Trudeau Mc et al.; *Science* 1995 269 92-95, and Sanguinetti M C et al.; *Cell* 1995 81 299-307.

In another preferred embodiment the ERG channel is a mouse (*Mus musculus*) ERG1 channel as the one cloned by London B et al.; *Circ. Res.* 1997 81 870-878.

In a third preferred embodiment the ERG channel is a rat (*Rattus norvegicus*) ERG 1 channel as the one cloned by Bauer C K et al.; *Receptors Channels* 1998 6 19-29.

In a fourth preferred embodiment the ERG channel is an insect (*Drosophila melanogaster*) ERG1 channel as the one cloned by Titus S et al.; *J. Neurosci.* 1997 17 875-881.

In a fifth preferred embodiment the ERG channel is a canine (*Canis familiaris*) ERG1 channel as the one cloned by Zehelein J et al.; *Eur. J. Physiol.* 2001 442 875-881.

In a sixth preferred embodiment the ERG channel is a horse (*Equus caballus*) ERG1 channel as the one cloned by Finley M R et al.; *Am. J. Physiol. Heart Circ. Physiol.* 2002 283 H126-H138.

Determination of the ability of a compound to activate the ERG channel may be determined on an ERG channel alone or on an ERG channel forming a complex with KCNE1, and/or KCNE2, and/or other accessory proteins. KCNE1 also is called mink, and KCNE2 also is called mirP, and are described by Abbott G W et al.; *Cell* 1999 97 175-187.

Determination of the ability of a compound to activate the ERG channel may in particular be accomplished by any conventional electrophysiological method, and preferably by patch clamp technology, e.g. as described in the working examples.

Cardiac Diseases

The present invention relates to the use of ERG channel opening compounds for the treatment, prevention or alleviation of a cardiac disease, disorder or condition. In the context of this invention a cardiac disease, disorder or condition is any disease, disorder or condition associated with an abnormal rhythm of the heart.

In a more specific embodiment a cardiac disease, disorder or condition of the invention is cardiac arrhytmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, or any other abnormal rhythm, e.g. caused by myocardial ischaemia, myocardial infarction, cardiac hypertrophy, cardiomyopathy or a genetic disease.

In another specific embodiment a cardiac disease, disorder or condition is cardiac ishemia, ishcemic heart disease, hypertrophic heart, cardiomyopathia or ailing heart.

In a more preferred embodiment a cardiac disease, disorder or condition of the invention is cardiac arrhythmia, atrial fibrillation and/or ventricular tachyarrhythmia.

In a most preferred embodiment a cardiac disease, disorder or condition of the invention is cardiac arrhythmia.

ERG Channel Activators

Viewed from another aspect the invention relates to the use of a therapeutically effective amount of a compound capable of activating an ERG channel, in particular the human ERG1 channel (Human Ether-a-go-go Related Gene channel, HERG1 channel).

Preferred ERG channel activating compounds for use according to the invention are the urea derivatives described in e.g. WO 94/22807, WO 96/25157, WO 97/45400, WO 97/45111, WO 98/47879, WO 2000/24707 and WO 2004/022529.

In a more preferred embodiment the ERG channel activating compound for use according to the invention is a diphenyl urea derivative of Formula I,

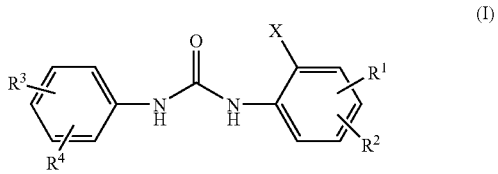

or an enantiomer or a mixture of its enantiomers, or a pharmaceutically acceptable salt thereof, wherein X represents hydroxy, alkoxy, amino, carboxy, alkyl-carbonyl, hydroxyaminocarbonyl, sulfamoyl, N-alkyl-sulfamoyl, N,N-di-alkyl-sulfamoyl, tetrazolyl, 2,4-dihydro-[1,2,4]triazol-3-one, 4H-[1,2,4]oxadiazol-5-one, or 1,2-dihydro-[1,2,4]triazol-3-one; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In an even more preferred embodiment the ERG channel activating compound for use according to the invention is a diphenyl urea derivative of Formula I, wherein X represents OH, alkoxy, carboxy, alkyl-carbonyl or tetrazolyl; and at least one of $R^1$, $R^2$, $R^3$ and $R^4$, independently of each other, represent halo, hydroxy, alkyl, alkoxy, thioalkoxy, nitro, cyano, haloalkyl, haloalkoxy, amino, acyl, alkoxy-carbonyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, and alkoxy-carbonyl; and the remainder of $R^1$, $R^2$, $R^3$ and $R^4$ represent hydrogen.

In a yet more preferred embodiment the ERG channel activating compound for use according to the invention is a diphenyl urea derivative of Formula I, wherein X represents hydroxy, amino, carboxy, hydroxyaminocarbonyl, sulfamoyl, tetrazolyl, 2,4-dihydro-[1,2,4]triazol-3-one, 4H-[1,2,4]oxadiazol-5-one, or 1,2-dihydro-[1,2,4]triazol-3-one; and at least one of $R^1$, $R^2$, $R^3$ and $R^4$, and independently of each other, represent halo, hydroxy, alkyl, alkoxy, nitro, haloalkyl, haloalkoxy, amino, alkoxy-carbonyl-alkenyl, N-(alkyl-carbonyl)amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with a substituent selected from the group consisting of halo, haloalkyl, haloalkoxy, carbamoyl, N-alkyl-carbamoyl, N,N-di-alkyl-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a second preferred embodiment the ERG channel activating compound for use according to the invention is a diphenyl urea derivative of Formula I, wherein X represents hydroxy; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents hydroxy; and at least one of $R^1$, $R^2$, $R^3$ and $R^4$, independently of each other, represent halo, hydroxy, alkyl, alkoxy, nitro, haloalkyl, haloalkoxy, acyl, alkoxy-carbonyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkoxy, acyl, alkoxy-carbonyl and haloalkyl; and the remainder of $R^1$, $R^2$, $R^3$ and $R^4$ represent hydrogen.

In a most preferred embodiment the ERG channel activating urea derivative for use according to the invention is 1-(3-Trifluoromethyl-phenyl)-3-(2-hydroxy-phenyl)-urea;

1-(3-Trifluoromethyl-phenyl)-3-(2-hydroxy-3-nitro-phenyl)-urea;

1-(3-Trifluoromethyl-phenyl)-3-(2,4-dihydroxy-phenyl)-urea;

1-(3-Trifluoromethyl-phenyl)-3-(2-hydroxy-4-methoxyphenyl)-urea;

1-(3-Trifluoromethyl-phenyl)-3-(2-hydroxy-4-methoxycarbonyl-5-chlorophenyl)-urea;

1-(3-Trifluoromethyl-phenyl)-3-(2-hydroxy-4-methoxycarbonyl-phenyl)-urea;

1-(3-Trifluoromethyl-phenyl)-3-(2-hydroxy-4-chlorophenyl)-urea;

1-(3-Trifluoromethyl-phenyl)-3-(2,5-dihydroxy-phenyl)-urea;

1-(3-Trifluoromethyl-phenyl)-3-(2-hydroxy-5-chlorophenyl)-urea;

1-(3-Trifluoromethoxy-phenyl)-3-(2-hydroxy-5-chlorophenyl)-urea;

1-(3-Trifluoromethyl-phenyl)-3-(2-hydroxy-5-methoxycarbonyl-phenyl)-urea;

1-(3-Trifluoromethyl-phenyl)-3-(2-hydroxy-5-nitro-phenyl)-urea;

1-(3-Trifluoromethyl-phenyl)-3-(2-hydroxy-5-methoxyphenyl)-urea;

1-(3-Carboxy-phenyl)-3-(2-hydroxy-5-chloro-phenyl)-urea;

1-(3-Hydroxy-phenyl)-3-(2-hydroxy-5-chloro-phenyl)-urea;

1-(3-Methoxycarbonyl-phenyl)-3-(2-hydroxy-5-chloro-phenyl)-urea;
1-(3-Methyl-phenyl)-3-(2-hydroxy-5-chloro-phenyl)-urea;
1-(3-Nitro-phenyl)-3-(2-hydroxy-5-chloro-phenyl)-urea;
1-(3-Trifluoromethyl-phenyl)-3-(2-hydroxy-6-nitro-phenyl)-urea;
1-[4-(N-ethyl-sulfamoyl)-phenyl]-3-(2-hydroxy-5-chloro-phenyl)-urea;
1,3-Bis-(2-hydroxy-5-trifluoromethyl-phenyl)-urea;
1-(3-Trifluoromethyl-phenyl)-3-(2-hydroxy-5-trifluoromethyl-phenyl)-urea;
1-(2-Trifluoromethyl-phenyl)-3-(2-hydroxy-5-trifluoromethyl-phenyl)-urea;
1-(3-Trifluoromethyl-phenyl)-3-(2,6-dihydroxy-phenyl)-urea;
1-(4-Chloro-phenyl)-3-(2-hydroxy-4-methoxy-phenyl)-urea;
1-(3-Trifluoromethyl-phenyl)-3-(2-hydroxy-5-bromo-phenyl)-urea; or
1-(2-Trifluoromethyl-phenyl)-3-(2-hydroxy-5-chloro-phenyl)-urea;
or a pharmaceutically acceptable salt thereof.

In a third preferred embodiment the ERG channel activating compound for use according to the invention is a diphenyl urea derivative of Formula I, wherein X represents carboxy; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents carboxy; and at least one of $R^1$, $R^2$, $R^3$ and $R^4$, independently of each other, represent halo, hydroxy, alkyl, alkoxy, nitro, haloalkyl, haloalkoxy, acyl, alkoxy-carbonyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkoxy, acyl, alkoxy-carbonyl and haloalkyl; and the remainder of $R^1$, $R^2$, $R^3$ and $R^4$ represent hydrogen.

In an even more preferred embodiment X represents carboxy; and at least one of $R^1$, $R^2$, $R^3$ and $R^4$, and independently of each other, represent halo, hydroxy, alkyl, alkoxy, nitro, haloalkyl, haloalkoxy, and/or phenyl.

In a most preferred embodiment the ERG channel activating urea derivative or use according to the invention is
1-Phenyl-3-(2-carboxy-phenyl)-urea;
1-(2-Methoxy-phenyl)-3-(2-carboxy-phenyl)-urea;
1-(2-Trifluoromethyl-phenyl)-3-(2-carboxy-phenyl)-urea;
1-(3-Methoxy-phenyl)-3-(2-carboxy-phenyl)-urea;
1-(3-Nitro-phenyl)-3-(2-carboxy-phenyl)-urea;
1-(3-Trifluoromethyl-phenyl)-3-(2-carboxy-phenyl)-urea;
1-(4-Methoxy-phenyl)-3-(2-carboxy-phenyl)-urea;
1-(4-Bromo-phenyl)-3-(2-carboxy-phenyl)-urea;
1-(4-Nitro-phenyl)-3-(2-carboxy-phenyl)-urea;
1-(3-Trifluoromethyl-phenyl)-3-(2-carboxy-3-methyl-phenyl)-urea;
1-(3-Trifluoromethyl-phenyl)-3-(2-carboxy-4-methyl-phenyl)-urea;
1-(3-Trifluoromethyl-phenyl)-3-(2-carboxy-4-hydroxy-phenyl)-urea;
1-(3-Trifluoromethyl-phenyl)-3-(2-carboxy-4-nitro-phenyl)-urea;
1-(3-Trifluoromethyl-phenyl)-3-(2-carboxy-4-methoxy-phenyl)-urea;
1-(3-Trifluoromethyl-phenyl)-3-(2-carboxy-4-bromo-phenyl)-urea;
1-(3-Trifluoromethyl-phenyl)-3-(2-carboxy-4-fluoro-phenyl)-urea;
1-(3-Trifluoromethyl-phenyl)-3-(2-carboxy-4,5-dimethoxy-phenyl)-urea;
1-(3-Trifluoromethyl-phenyl)-3-(2-carboxy-5-nitro-phenyl)-urea;
1-(3-Trifluoromethyl-phenyl)-3-(2-carboxy-5-trifluoromethyl-phenyl)-urea;
1-(3-Trifluoromethyl-phenyl)-3-(2-carboxy-6-methyl-phenyl)-urea;
1-(3-Trifluoromethyl-phenyl)-3-(2-carboxy-5-nitro-phenyl)-urea;
1-(3,5-Bis-trifluoromethyl-phenyl)-3-(2-carboxy-5-chloro-phenyl)-urea;
1-(4-Chloro-phenyl)-3-(2-carboxy-3-iodo-phenyl)-urea;
1-(2-Fluoro-phenyl)-3-(2-carboxy-5-chloro-phenyl)-urea;
1-(4-Chloro-phenyl)-3-(2-carboxy-5-chloro-phenyl)-urea;
1-(3-Trifluoromethyl-phenyl)-3-(2-carboxy-4-methyl-phenyl)-urea;
1-(3-Trifluoromethyl-phenyl)-3-(2-carboxy-4-bromo-phenyl)-urea;
1-(3,5-Dimethoxy-phenyl)-3-(2-carboxy-4-bromo-phenyl)-urea;
1-(4-Biphenyl)-3-(2-carboxy-phenyl)-urea; or
1-(2-Methoxy-phenyl)-3-(2-carboxy-5-chloro-phenyl)-urea;
or a pharmaceutically acceptable salt thereof.

In a fourth preferred embodiment the ERG channel activating compound for use according to the invention is a diphenyl urea derivative of Formula I, wherein X represents tetrazolyl; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents 1H-tetrazolyl; and at least one of $R^1$, $R^2$, $R^3$ and $R^4$, independently of each other, represent halo, hydroxy, alkyl, alkoxy, nitro, haloalkyl, haloalkoxy, acyl, alkoxy-carbonyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, and alkoxy-carbonyl; and the remainder of $R^1$, $R^2$, $R^3$ and $R^4$ represent hydrogen.

In an even more preferred embodiment X represents 1H-tetrazolyl; and at least one of $R^1$, $R^2$, $R^3$ and $R^4$, and independently of each other, represent Cl, Br, F, hydroxy, alkyl, alkoxy, nitro, $CF_3$, $OCF_3$, amino, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with a substituent selected from the group consisting of Cl, Br, F, $CF_3$, $OCF_3$, carbamoyl, N-alkyl-carbamoyl, N,N-di-alkyl-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a most preferred embodiment the ERG channel activating urea derivative for use according to the invention is 1-(3-Biphenyl)-3-[2-(1H-tetrazol-5-yl)-phenyl]-urea;

1-(3-Acetyl-phenyl)-3-[2-(1H-tetrazol-5-yl)-phenyl]-urea;

1-(4-Biphenyl)-3-[2-(1H-tetrazol-5-yl)-phenyl]-urea;

1-(2-Bromo-phenyl)-3-[2-(1H-tetrazol-5-yl)-4-bromo-phenyl]-urea;

1-(2-Chloro-phenyl)-3-[2-(1H-tetrazol-5-yl)-4-bromo-phenyl]-urea;

1-(2-Fluoro-phenyl)-3-[2-(1H-tetrazol-5-yl)4-bromo-phenyl]-urea;

1-(2-Methyl-phenyl)-3-[2-(1H-tetrazol-5-yl)4-bromo-phenyl]-urea;

1-(2-Ethyl-phenyl)-3-[2-(1H-tetrazol-5-yl)-4-bromo-phenyl]-urea;

1-(2-Nitro-phenyl)-3-[2-(1H-tetrazol-5-yl)-4-bromo-phenyl]-urea;

1-(2-Trifluoromethyl-phenyl)-3-[2-(1H-tetrazol-5-yl)-4-bromo-phenyl]-urea;

1-(3-Acetyl-phenyl)-3-[2-(1H-tetrazol-5-yl)-4-bromo-phenyl]-urea;

1-(3-Biphenyl)-3-[2-(1H-tetrazol-5-yl)4-bromo-phenyl]-urea;

1-(3-Bromo-phenyl)-3-[2-(1H-tetrazol-5-yl)4-bromo-phenyl]-urea;

1-(3-Chloro-phenyl)-3-[2-(1H-tetrazol-5-yl)4-bromo-phenyl]-urea;

1-(3-Fluoro-phenyl)-3-[2-(1H-tetrazol-5-yl)4-bromo-phenyl]-urea;

1-(3-Methyl-phenyl)-3-[2-(1H-tetrazol-5-yl)-4-bromo-phenyl]-urea;

1-(3-Methoxy-phenyl)-3-[2-(1H-tetrazol-5-yl)-4-bromo-phenyl]-urea;

1-(3-Nitro-phenyl)-3-[2-(1H-tetrazol-5-yl)-4-bromo-phenyl]-urea;

1-(3-Trifluoromethyl-phenyl)-3-[2-(1H-tetrazol-5-yl)-4-bromo-phenyl]-urea;

1-(3,4-Dichloro-phenyl)-3-[2-(1H-tetrazol-5-yl)-4-bromo-phenyl]-urea;

1-(3-Nitro-4-methyl-phenyl)-3-[2-(1H-tetrazol-5-yl)-4-bromo-phenyl]-urea;

1-(3-Trifluoromethyl-4-chloro-phenyl)-3-[2-(1H-tetrazol-5-yl)-4-bromo-phenyl]-urea;

1-(3,5-Dichloro-phenyl)-3-[2-(1H-tetrazol-5-yl)-4-bromo-phenyl]-urea;

1-[3,5-Bis-trifluoromethyl-phenyl]-3-[4-bromo-2-(1H-tetrazol-5-yl)-phenyl]-urea;

1-(3,5-Dimethyl-phenyl)-3-[2-(1H-tetrazol-5-yl)-4-bromo-phenyl]-urea;

1-(4-Bromo-phenyl)-3-[2-(1H-tetrazol-5-yl)-4-bromo-phenyl]-urea;

1-(4-Ethoxyo-phenyl)-3-[2-(1H-tetrazol-5-yl)-4-bromo-phenyl]-urea;

1-(4-Methoxy-phenyl)-3-[2-(1H-tetrazol-5-yl)-4-bromo-phenyl]-urea;

1-(4-Methyl-phenyl)-3-[2-(1H-tetrazol-5-yl)-4-bromo-phenyl]-urea;

1-(4-Nitro-phenyl)-3-[2-(1H-tetrazol-5-yl)-4-bromo-phenyl]-urea;

1-(4-Trifluoromethyl-phenyl-3-[2-(1H-tetrazol-5-yl)-4-bromo-phenyl]-urea;

1-[4-(2-Propyl)-phenyl]-3-[2-(1H-tetrazol-5-yl)-4-bromo-phenyl]-urea;

1-(3-Trifluoromethyl-phenyl)-3-[2-(1H-tetrazol-5-yl)-4-amino-phenyl]-urea;

I -(3-Bromo-phenyl)-3-[2-(1H-tetrazol-5-yl)-4-biphenyl]-urea;

1-(3-Bromo-phenyl)-3-[2-(1H-tetrazol-5-yl)4-(3'-nitro)-biphenyl]-urea;

1-(3-Trifluoromethyl-phenyl)-3-[2-(1H-tetrazol-5-yl)-4-(3'-nitro)-biphenyl]-urea;

1-(3-Trifluoromethyl-phenyl)-3-[2-(1H-tetrazol-5-yl)-4-(4'-trifluoromethyl)-biphenyl]-urea;

1-(3-Trifluoromethyl-phenyl)-3-[2-(1H-tetrazol-5-yl)-4-(4'-ethoxycarbonyl)-biphenyl]-urea;

1-(3-Trifluoromethyl-phenyl)-3-[2-(1H-tetrazol-5-yl)-4-(4'-carboxy)-biphenyl]-urea;

1-(3,5-Bis-trifluoromethyl-phenyl)-3-[2-(1H-tetrazol-5-yl)-4-(4'-N,N-dimethyl-sulfamoyl)-biphenyl]-urea;

1-(3-Fluoro-5-trifluoromethyl-phenyl)-3-[2-(1H-tetrazol-5-yl)4-(4'-N,N-dimethyl-sulfamoyl)-biphenyl]-urea;

1-(3,5-Bis-trifluoromethyl-phenyl)-3-[2-(1H-tetrazol-5-yl)-4-(4'-N,N-dimethyl-carbamoyl)-biphenyl]-urea;

1-(3,5-Difluoro-phenyl)-3-[2-(1H-tetrazol-5-yl)-4-(3'-trifluoromethyl-biphenyl]-urea;

1-(3,5-Dichloro-phenyl)-3-[2-(1H-tetrazol-5-yl)-4-(4'-N,N-dimethyl-sulfamoyl)-biphenyl]-urea;

1-(3,5-Bis-trifluoromethyl-phenyl)-3-[2-(1H-tetrazol-5-yl)-4,6-dichloro-phenyl]-urea;

1-(3-Chloro-4-trifluoromethyl-phenyl)-3-[2-(1H-tetrazol-5-yl)-4-(2-N,N-dimethylcarbamoyl-ethyl)-phenyl]-urea;

1-(3-Trifluoromethyl-phenyl)-3-[2-(1H-tetrazol-5-yl)-4-amino-phenyl]-urea;

1-(4-Chloro-3-trifluoromethyl-phenyl)-3-[2-(1H-tetrazol-5-yl)-4-chloro-phenyl]-urea;

1-(3,5-Bis-trifluoromethyl-phenyl)-3-[2-(1H-tetrazol-5-yl)-4-(N-carboxy-methyl)-carbamoyl-phenyl]-urea;

1-(3,5-Bis-trifluoromethyl-phenyl)-3-[2-(1H-tetrazol-5-yl)-4-(2-N,N-dimethyl-carbamoyl-ethenyl)-phenyl]-urea;

1-(4-Fluoro-3-trifluoromethyl-phenyl)-3-[2-(1H-tetrazol-5-yl)-4-bromo-phenyl]-urea;

1-(3,5-Bis-trifluoromethyl-phenyl)-3-[2-(1H-tetrazol-5-yl)-4-bromo-phenyl]-urea;

1-(3,5-Bis-trifluoromethyl-phenyl)-3-[2-(1H-tetrazol-5-yl)-4-chloro-phenyl]-urea;

1-(3-Trifluoromethyl-phenyl)-3-[2-(1H-tetrazol-5-yl)-4-bromo-phenyl]-urea;

1-(3,5-Bis-trifluoromethyl-phenyl)-3-[2-(1H-tetrazol-5-yl)-4-(2-methoxy-carbonyl-ethenyl)-phenyl]-urea;

1-(3-Chloro-4-fluoro-phenyl)-3-[2-(1H-tetrazol-5-yl)4-bromo-phenyl]-urea;

1-(3,5-Dichloro-phenyl)-3-[2-(1H-tetrazol-5-yl)4-chloro-phenyl]-urea;

1-(4-Biphenyl)-3-[2-(1H-tetrazol-5-yl)-5-chloro-phenyl]-urea;

1-(4-Chloro-3-trifluoromethyl-phenyl)-3-[2-(1H-tetrazol-5-yl)-5-chloro-phenyl]-urea;

1-(3-Trifluoromethyl-phenyl)-3-[2-(1H-tetrazol-5-yl)-4-(methyl-carbonyl-amino)-phenyl]-urea; or 1-(2-Trifluoromethyl-phenyl)-3-[2-(1H-tetrazol-5-yl)-4-(4'-chloro-biphenyl)]-urea;

or a pharmaceutically acceptable salt thereof.

In a fifth preferred embodiment the ERG channel activating compound for use according to the invention is a diphenyl urea derivative of Formula I, wherein X represents 2,4-dihydro-[1,2,4]triazol-3-one; and at least one of $R^1$, $R^2$, $R^3$ and $R^4$, and independently of one another, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents 2,4-dihydro-[1,2,4]triazol-3-one; and at least one of $R^1$, $R^2$, $R^3$ and $R^4$, and independently of one another, represent halo, haloalkyl, haloalkoxy, carbamoyl, N-alkyl-carbamoyl, N,N-di-alkyl-carbamoyl, sulfamoyl, N-alkyl-sulfamoyl, N,N-di-alkyl-sulfamoyl and/or phenyl, which phenyl may optionally be substituted with a substituent selected from the group consisting of halo, haloalkyl, haloalkoxy, carbamoyl, N-alkyl-carbamoyl, N,N-di-alkyl-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a most preferred embodiment the ERG channel activating urea derivative for use according to the invention is 1-(3-Trifluoromethyl-phenyl)-3-[2-(5-oxo-4,5-dihydro-1H-[1,2,4]triazol-3-yl)-4-(4'-N,N-dimethyl-carbamoyl )-biphenyl]-urea;

or a pharmaceutically acceptable salt thereof.

In a sixth preferred embodiment the ERG channel activating compound for use according to the invention is a diphenyl urea derivative of Formula I, wherein X represents 4H-[1,2,4]oxadiazol-5-one; and at least one of $R^1$, $R^2$, $R^3$ and $R^4$, and independently of one another, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents 4H-[1,2,4]oxadiazol-5-one; and at least one of $R^1$, $R^2$, $R^3$ and $R^4$, and independently of one another, represent halo, haloalkyl, haloalkoxy, carbamoyl, N-alkyl-carbamoyl, N,N-di-alkyl-carbamoyl, sulfamoyl, N-alkyl-sulfamoyl, N,N-di-alkyl-sulfamoyl and/or phenyl, which phenyl may optionally be substituted with a substituent selected from the group consisting of halo, haloalkyl, haloalkoxy, carbamoyl, N-alkyl-carbamoyl, N,N-di-alkyl-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a most preferred embodiment the ERG channel activating urea derivative for use according to the invention is 1-(3-Trifluoromethyl-phenyl)-3-[2-(5-oxo-4,5-dihydro-[1,2,4]oxadiazol-3-yl)-4-(4'-N,N-dimethyl-carbamoyl)-biphenyl]-urea; or 1-(3-Trifluoromethyl-phenyl)-3-[2-(5-oxo-4,5-dihydro-[1,2,4]oxadiazol-3-yl)-5-chloro-phenyl]-urea;

or a pharmaceutically acceptable salt thereof.

In a seventh preferred embodiment the ERG channel activating compound for use according to the invention is a diphenyl urea derivative of Formula I, wherein X represents 1,2-dihydro-[1,2,4]triazol-3-one; and at least one of $R^1$, $R^2$, $R^3$ and $R^4$, and independently of one another, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents 1,2-dihydro-[1,2,4]triazol-3-one; and at least one of $R^1$, $R^2$, $R^3$ and $R^4$, and independently of one another, represent halo, haloalkyl, haloalkoxy, carbamoyl, N-alkyl-carbamoyl, N,N-di-alkyl-carbamoyl, sulfamoyl, N-alkyl-sulfamoyl, N,N-di-alkyl-sulfamoyl and/or phenyl, which phenyl may optionally be substituted with a substituent selected from the group consisting of halo, haloalkyl, haloalkoxy, carbamoyl, N-alkyl-carbamoyl, N,N-di-alkyl-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a most preferred embodiment the ERG channel activating urea derivative for use according to the invention is 1-(3-Trifluoromethyl-phenyl)-3-[2-(3-oxo-2,3-dihydro-[1,2,4]triazol-1-yl)-phenyl]-urea;

or a pharmaceutically acceptable salt thereof.

In an eight preferred embodiment the ERG channel activating compound for se according to the invention is a diphenyl urea derivative of Formula I, wherein X represents sulfamoyl, N-alkyl-sulfamoyl or N,N-di-alkyl-sulfamoyl; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment the ERG channel activating compound for use according to the invention is a diphenyl urea derivative of Formula I, wherein X represents sulfamoyl; and at least one of $R^1$, $R^2$, $R^3$ and $R^4$, and independently of each other, represent halo, $CF_3$, $OCF_3$; and the remainder of $R^1$, $R^2$, $R^3$ and $R^4$ represent hydrogen.

In a most preferred embodiment the ERG channel activating urea derivative for use according to the invention is
1-(3-Trifluoromethyl-phenyl)-3-(2-sulfamoyl-5-chloro-phenyl)-urea;
or a pharmaceutically acceptable salt thereof.

In a ninth preferred embodiment the ERG channel activating compound for use according to the invention is a diphenyl urea derivative of Formula I, wherein X represents hydroxyaminocarbonyl; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents hydroxyaminocarbonyl; and at least one of $R^1$, $R^2$, $R^3$ and $R^4$, and independently of each other, represent halo, $CF_3$, $OCF_3$; and the remainder of $R^1$, $R^2$, $R^3$ and $R^4$ represent hydrogen.

In a most preferred embodiment the ERG channel activating urea derivative for use according to the invention is
1-(3-Trifluoromethyl-phenyl)-3-[2-(hydroxy-amino-carbonyl)-phenyl]-urea;
or a pharmaceutically acceptable salt thereof.

In a tenth preferred embodiment the ERG channel activating compound for use according to the invention is a diphenyl urea derivative of Formula I, wherein X represents amino; and at least one of $R^1$, $R^2$, $R^3$ and $R^4$, and independently of each other, represent halo, hydroxy, alkyl, alkoxy, thioalkoxy, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl; and the remainder of $R^1$, $R^2$, $R^3$ and $R^4$ represent hydrogen.

In a more preferred embodiment X represents amino; and at least one of $R^1$, $R^2$, $R^3$ and $R^4$, and independently of each other, represent halo, $CF_3$, $OCF_3$; and the remainder of $R^1$, $R^2$, $R^3$ and $R^4$ represent hydrogen.

In a most preferred embodiment the ERG channel activating urea derivative for use according to the invention is
1-(3-Trifluoromethyl-phenyl)-3-(2-amino-5-chloro-phenyl)-urea;
or a pharmaceutically acceptable salt thereof.

In an eleventh preferred embodiment the ERG channel activating compound for use according to the invention is a diphenyl urea derivative of Formula II, wherein (II)

or an enantiomer or a mixture of its enantiomers, or a pharmaceutically acceptable salt thereof, wherein X represents hydroxy, carboxy, amino, hydroxyaminocarbonyl, sulfamoyl or 1H-tetrazol-5-yl; and at least one of $R^1$, $R^2$, $R^3$ and $R^4$, and independently of each other, represent halo and/or haloalkyl; and the remainder of $R^1$, $R^2$, $R^3$ and $R^4$ represent hydrogen.

In a most preferred embodiment the ERG channel activating urea derivative for use according to the invention is
1-(3-Trifluoromethyl-phenyl)-3-(2-hydroxy-5-chloro-phenyl)-urea;
1-(3,5-Bis-trifluoromethyl-phenyl)-3-[4-bromo-2-(1H-tetrazol-5-yl)-phenyl]-urea;
1,3-Bis-(2-hydroxy-5-trifluoromethyl-phenyl)-urea;
1-(3,5-Difluoro-phenyl)-3-[2-(1H-tetrazol-5-yl)-4-(3'-trifluoromethyl-biphenyl]-urea;
1-(3,5-Bis-trifluoromethyl-phenyl)-3-(2-carboxy-5-chloro-phenyl)-urea;
1-(3,5-Bis-trifluoromethyl-phenyl)-3-[2-(1H-tetrazol-5-yl)-4,6-dichloro-phenyl]-urea;
1-(3-Trifluoromethyl-phenyl)-3-(2-sulfamoyl -5-chloro-phenyl)-urea;
1-(4-Chloro-phenyl)-3-(2-carboxy-3-iodo-phenyl)-urea;
1-(2-Fluoro-phenyl)-3-(2-carboxy-5-chloro-phenyl)-urea;
1-(3-Trifluoromethyl-phenyl)-3-(2-hydroxy-5-trifluoromethyl-phenyl)-urea;
1-(4-Chloro-phenyl)-3-(2-carboxy-5-chloro-phenyl)-urea;
1-(3-Trifluoromethyl-phenyl)-3-(2-carboxy-4-methyl-phenyl)-urea;
1-(2-Trifluoromethyl-phenyl)-3-(2-hydroxy-5-trifluoromethyl-phenyl)-urea;
1-(3-Trifluoromethyl-phenyl)-3-[2-(hydroxy-amino-carbonyl)-phenyl]-urea;

1-(4-Chloro-3-trifluoromethyl-phenyl)-3-[2-(1H-tetrazol-5-yl)-4-chloro-phenyl]-urea;

1-(3-Trifluoromethyl-phenyl)-3-(2-amino-5-chloro-phenyl)-urea;

1-(3-Trifluoromethyl-phenyl)-3-(2-hydroxy-5-bromo-phenyl)-urea;

1-(2-Trifluoromethyl-phenyl)-3-(2-hydroxy-5-chloro-phenyl)-urea;

1-(4-Fluoro-3-trifluoromethyl-phenyl)-3-[2-(1H-tetrazol-5-yl)-4-bromo-phenyl]-urea;

1-(3,5-Bis-trifluoromethyl-phenyl)-3-[2-(1H-tetrazol-5-yl)4-bromo-phenyl]-urea;

1-(3,5-Bis-trifluoromethyl-phenyl)-3-[2-(1H-tetrazol-5-yl)4-chloro-phenyl]-urea;

1-(3-Trifluoromethyl-phenyl)-3-[2-(1H-tetrazol-5-yl)4-bromo-phenyl]-urea;

1-(3-Chloro-4-fluoro-phenyl)-3-[2-(1H-tetrazol-5-yl)-4-bromo-phenyl]-urea;

1-(3,5-Dichloro-phenyl)-3-[2-(1H-tetrazol-5-yl)-4-chloro-phenyl]-urea;

1-(3,5-Dichloro-phenyl)-3-[2-(1H-tetrazol-5-yl)-4-bromo-phenyl]-urea; or 1-(4-Chloro-3-trifluoromethyl-phenyl)-3-[2-(1H-tetrazol-5-yl)-5-chloro-phenyl]-urea;

or a pharmaceutically acceptable salt thereof.

In a twelfth preferred embodiment the ERG channel activating compound for use according to the invention is a diphenyl urea derivative of Formula II,

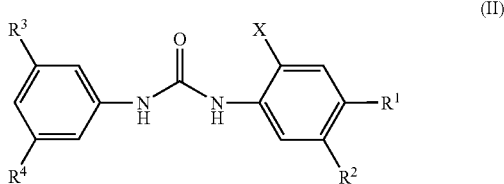

(II)

or an enantiomer or a mixture of its enantiomers, or a pharmaceutically acceptable salt thereof, wherein X represents hydroxy, carboxy or 1H-tetrazol-5-yl; and at least one of $R^1$, $R^2$, $R^3$ and $R^4$, independently of each other, represent halo and/or haloalkyl; and the remainder of $R^1$, $R^2$, $R^3$ and $R^4$ represent hydrogen.

In a most preferred embodiment the ERG channel activating urea derivative for use according to the invention is 1-(3-Trifluoromethyl-phenyl)-3-(2-hydroxy-5-chloro-phenyl)-urea;

1-(3,5-Bis-trifluoromethyl-phenyl)-3-[4-bromo-2-(1H-tetrazol-5-yl)-phenyl]-urea; or 1,3-Bis-(2-hydroxy-5-trifluoromethyl-phenyl)-urea;

or a pharmaceutically acceptable salt thereof.

In a thirteenth preferred embodiment the ERG channel activating compound for use according to the invention is a urea derivative of Formula III,

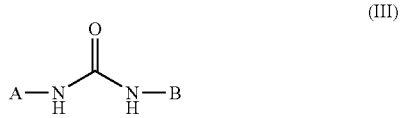

(III)

or an enantiomer or a mixture of its enantiomers, or a pharmaceutically acceptable salt thereof, or an N oxide thereof, wherein A and B, independently of each other, represent a monocyclic carbocyclic or heterocyclic group, optionally substituted with one or more of X, $R^1$ and/or $R^2$, wherein X represents hydroxy, alkoxy, amino, carboxy, alkylcarbonyl, hydroxyaminocarbonyl, sulfamoyl, N-alkyl-sulfamoyl, N,N-di-alkyl-sulfamoyl, tetrazolyl, 2,4-dihydro-[1,2,4]triazol-3-one, 4H-[1,2,4]oxadiazol-5-one, or 1,2-dihydro-[1,2,4]triazol-3-one; and $R^1$ and $R^2$, independently of each other, represent halo, hydroxy, alkyl, alkoxy, thioalkoxy, oxo, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl and/or phenyl, which phenyl may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl.

In a more preferred embodiment A represents a monocyclic carbocyclic group selected from cyclohexyl and phenyl, which monocyclic carbocyclic group is optionally substituted with $R^1$ and/or $R^2$; and B represents phenyl or a monocyclic heterocyclic group selected from pyridyl, pyridazinyl, pyrimidinyl or pyrazinyl, or an N oxide thereof, which carbocyclic or heterocyclic group is optionally substituted with one or more of X, $R^1$ and/or $R^2$.

In an even more preferred embodiment A represents phenyl, which is optionally substituted with $R^1$ and/or $R^2$; and B represents pyridyl or pyrimidinyl, or an N oxide thereof, which carbocyclic or heterocyclic group is optionally substituted with one or more of X, $R^1$ and/or $R^2$.

In another preferred embodiment A represents pyridyl, optionally substituted with $R^1$ and/or $R^2$; and B represents phenyl or a monocyclic heterocyclic group selected from pyridyl, pyridazinyl, pyrimidinyl or pyrazinyl, or an N oxide thereof, which carbocyclic or heterocyclic group is optionally substituted with one or more of X, $R^1$ and/or $R^2$.

In a more preferred embodiment X represents hydroxy, carboxy or tetrazolyl.

In an even more preferred embodiment $R^1$ and $R^2$, independently of each other, represent halo, hydroxy, alkyl, alkoxy, thioalkoxy, oxo, nitro, cyano, haloalkyl, haloalkoxy, amino, carboxy and/or alkoxy-carbonyl.

In a most preferred embodiment the ERG channel activating urea derivative for use according to the invention is 1-Pyrimidin-2-yl-3-(3-trifluoromethyl-phenyl)-urea;

1-(2-Hydroxy-6-methoxy-pyridin-3-yl)-3-(3-fluoromethyl-phenyl)-urea;

1-(1-Oxy-pyridin-2-yl)-3-(3-trifluoromethyl-phenyl)-urea;

1-(3,5-Dihydroxy-phenyl)-3-(3-trifluoromethyl-phenyl)-urea;

1(1,2,3,6-Tetrahydro-2,6-dioxo-4-carboxy-pyrimidin-5-yl)-3-(3-trifluoromethyl-phenyl)-urea;

1-(2-Carboxy-pyrazin-3-yl)-3-(3-trifluoromethyl-phenyl)-urea;

1-[2-(1H-tetrazol-5-yl)-phenyl]-3-phenyl-urea;

1-(2-Carboxy-5-chloro-phenyl)-3-cyclohexyl-urea;

1-(3-Carboxy-pyridin-2-yl)-3-(2-chloro-pyridin-3-yl)-urea;

1-(2-Chloro-pyridin-3-yl)-3-(2-carboxy-5-chloro-phenyl)-urea;

1-(3-Carboxy-5-chloro-pyridin-2-yl)-3-(3,5-dichloro-phenyl)-urea;
or a pharmaceutically acceptable salt thereof.

In a fourteenth preferred embodiment the ERG channel activating compound for use according to the invention is a benzamide derivative of Formula IV,

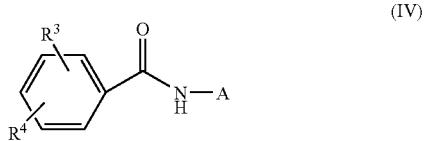

(IV)

or an enantiomer or a mixture of its enantiomers, or a pharmaceutically acceptable salt thereof, wherein A represents a monocyclic carbocyclic or heterocyclic group, optionally substituted with one or more of X, $R^1$ and/or $R^2$, wherein X represents hydroxy, alkoxy, amino, carboxy, alkyl-carbonyl, hydroxyaminocarbonyl, sulfamoyl, N-alkyl-sulfamoyl, N,N-di-alkyl-sulfamoyl, tetrazolyl, 2,4-dihydro-[1,2,4]triazol-3-one, 4H-[1,2,4]oxadiazol-5-one, or 1,2-dihydro-[1,2,4]triazol-3-one; and $R^1$, $R^2$, $R^3$ and $R^4$, independently of each other, represent halo, hydroxy, alkyl, alkoxy, thioalkoxy, oxo, nitro, cyano, haloalkyl, haloalkoxy, amino, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, N,N-di-alkyl-sulfamoyl phenyl and/or anilino, which phenyl or anilino may optionally be substituted with one or two substituents selected from the group consisting of halo, hydroxy, alkyl, alkoxy, nitro, haloalkyl, haloalkoxy, acyl, alkoxy-carbonyl, alkoxy-carbonyl-alkyl, alkoxy-carbonyl-alkenyl, N-(alkyl-carbonyl)-amino, carbamoyl, N-alkyl-carbamoyl, N,N-di-alkyl-carbamoyl, N,N-di-alkyl-carbamoyl-alkyl, N,N-di-alkyl-carbamoyl-alkenyl, N-(carboxy-alkyl)-carbamoyl, sulfamoyl, N-alkyl-sulfamoyl, and N,N-di-alkyl-sulfamoyl.

In a more preferred embodiment A represents phenyl or pyridinyl, optionally substituted with one or more of X, $R^1$ and/or $R^2$.

In an even preferred embodiment X represents hydroxy, carboxy or tetrazolyl.

In a yet more preferred embodiment $R^1$, $R^2$, $R^3$ and $R^4$, independently of each other, represent halo, hydroxy, alkyl, alkoxy, thioalkoxy, oxo, nitro, cyano, haloalkyl, haloalkoxy, amino, carboxy and/or alkoxy-carbonyl, phenyl and/or anilino, which phenyl or anilino may optionally be substituted with one or two substituents selected from the group consisting of halo, haloalkyl, and haloalkoxy.

In a still more preferred embodiment $R^1$ and $R^2$, independently of each other, represent halo, hydroxy, nitro, $CF_3$, phenyl and/or anilino, which phenyl and anilino is optionally substituted with halo and/or $CF_3$; and $R^3$ and $R^4$, independently of each other, represent halo, hydroxy, nitro and/or $CF_3$.

In a most preferred embodiment the ERG channel activating benzamide derivative for use according to the invention is
N-[3-Chloro-4-(4-chloro-phenylamino)-phenyl]-2-hydroxy-5-nitro-benzamide;
N-[3-(1H-Tetrazol-5-yl)-biphenyl-4-yl]-3,5-bis-trifluoromethyl-benzamide;
or a pharmaceutically acceptable salt thereof.

In a further aspect the invention provides novel compounds useful as ERG channel activators.

In a preferred embodiment the compound of the invention is a urea derivative of Formula III, selected from the group consisting of
1-Pyrimidin-2-yl-3-(3-trifluoromethyl-phenyl)-urea;
1-(2-Hydroxy-6-methoxy-pyridin-3-yl)-3-(3-fluoromethyl-phenyl)-urea;
1-(1-Oxy-pyridin-2-yl)-3-(3-trifluoromethyl-phenyl)-urea;
2,6-Dioxo-5-[3-(3-trifluoromethyl-phenyl)-ureido]-1,2,3,6-tetrahydro-pyrimidine-4-carboxylic acid;
3-[3-(3-Trifluoromethyl-phenyl)-ureido]-pyrazine-2-carboxylic acid;
1-(2-Hydroxy-5-trifluoromethyl-phenyl)-3-(2-trifluoromethyl-phenyl)-urea
1-(5-Chloro-2-hydroxy-phenyl)-3-(2-trifluoromethyl-phenyl)-urea;
1-(3,5-Dihydroxy-phenyl)-3-(3-trifluoromethyl-phenyl)-urea;
4-Chloro-2-[3-(2-fluoro-phenyl)-ureido]-benzoic acid;
4-Chloro-2-[3-(3-trifluromethyl-phenyl)-ureido]-benzenesulfonamide;
1-(3-Chloro-4-trifluoromethyl-phenyl)-3-[2-(1H-tetrazol-5-yl)-4-(2-N,N-dimethylcarbamoyl-ethyl)-phenyl]-urea;
1-[4-Chloro-2-(1H-tetrazol-5-yl)-phenyl]-3-(3,5-dichloro-phenyl)-urea;
1-[4-Chloro-2-(1H-tetrazol-5-yl)-phenyl]-3-(4-chloro-3-trifluoromethyl-phenyl)-urea;
3'-(5-Oxo-4,5-dihydro-[1,2,4]oxadiazol-3-yl)-4'-[3-(3-trifluromethyl-phenyl)-ureido]-biphenyl-4-carboxylic acid dimethylamide; and
3'-(5-Oxo-4,5-dihydro-1H-[1,2,4]triazol-3-yl)4'-[3-(3-trifluromethyl-phenyl)-ureido]-biphenyl-4-carboxylic acid dimethylamide;
or a pharmaceutically acceptable salt thereof.

In another preferred embodiment the compound of the invention is a diphenyl urea derivative of Formula I, selected from the group consisting of
1-(2-Hydroxy-5-trifluoromethyl-phenyl)-3-(2-trifluoromethyl-phenyl)-urea;
1-(5-Chloro-2-hydroxy-phenyl)-3-(2-trifluoromethyl-phenyl)-urea;
1-(3,5-Dihydroxy-phenyl)-3-(3-trifluoromethyl-phenyl)-urea;
4-Chloro-2-[3-(2-fluoro-phenyl)-ureido]-benzoic acid;
4-Chloro-2-[3-(3-trifluromethyl-phenyl)-ureido]-benzenesulfonamide;
1-(3-Chloro-4-trifluoromethyl-phenyl)-3-[2-(1H-tetrazol-5-yl)-4-(2-N,N-dimethylcarbamoyl-ethyl)-phenyl]-urea;
1-[4-Chloro-2-(1H-tetrazol-5-yl)-phenyl]-3-(3,5-dichloro-phenyl)-urea;
1-[4-Chloro-2-(1H-tetrazol-5-yl)-phenyl]-3-(4-chloro-3-trifluoromethyl-phenyl)-urea;
3'-(5-Oxo-4,5-dihydro-[1,2,4]oxadiazol-3-yl)4'-[3-(3-trifluromethyl-phenyl)-ureido]-biphenyl-4carboxylic acid dimethylamide; and
3'-(5-Oxo-4,5-dihydro-1H-[1,2,4]triazol-3-yl)-4'-[3-(3-trifluromethyl-phenyl)-ureido]-biphenyl-4-carboxylic acid dimethylamide;
or a pharmaceutically acceptable salt thereof.

In a third preferred embodiment the compound of the invention is a benzamide derivative of Formula IV, selected from the group consisting of N-[3-Chloro-4-(4-chloro-phenylamino)-phenyl]-2-hydroxy-5-nitro-benzamide;
N-[3-(1H-Tetrazol-5-yl)-biphenyl-4-yl]-3,5-bis-trifluoromethyl-benzamide;
or a pharmaceutically acceptable salt thereof.

The compounds of the invention may be obtained as described in Example 5.

Definition of Substituents

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$alkyl; lower alkyl), including pentyl, isopentyl, neopentyl, tertiary pentyl, hexyl and iso-hexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkoxy group designates an "alkyl-O-" group, wherein alkyl is as defined above. Examples of preferred alkoxy groups of the invention include methoxy and ethoxy.

In the context of this invention an alkoxy-carbonyl group designates an "alkyl-O—(CO)—" group, wherein alkyl is as defined above. Examples of preferred alkoxy-carbonyl groups of the invention include methoxy-carbonyl and ethoxy-carbonyl.

In the context of this invention an alkoxy-carbonyl-alkyl group designates an "alkyl-O-(CO)-alkyl" group, wherein alkyl is as defined above. Examples of preferred alkoxy-carbonyl-alkyl groups of the invention include methoxy-carbonyl-methyl and ethoxy-carbonyl-methyl, methoxy-carbonyl-ethyl and ethoxy-carbonyl-ethyl.

In the context of this invention an alkoxy-carbonyl-alkenyl group designates an "alkyl-O-(CO)-alkenyl-" group, wherein alkyl and alkenyl are as defined above. Examples of preferred alkoxy-carbonyl-alkenyl groups of the invention include methoxy-carbonyl-ethenyl, ethoxy-carbonyl-ethenyl, methoxy-carbonyl-propenyl and ethoxy-carbonyl-propenyl.

In the context of this invention a thioalkoxy group designates an "alkyl-S-" group, wherein alkyl is as defined above.

In the context of this invention a haloalkyl group designates an alkyl group as defined herein, which alkyl group is substituted one or more times with halogen. Preferred haloalkyl groups of the invention include trihalogenmethyl and trihalogenethyl.

In the context of this invention a haloalkoxy group designates an alkoxy group as defined herein, which alkoxy group is substituted one or more times with halogen. Preferred haloalkoxy groups of the invention include trihalogenmethoxy, and trihalogenethoxy.

In the context of this invention an acyl group designates a carboxy group (—COOH) or an alkyl-carbonyl group (alkyl-CO-), wherein alkyl is as defined above. Examples of preferred acyl groups of the invention include carboxy, acetyl, and propionyl.

In the context of this invention a monocyclic carbocyclic group, holding carbon only as ring atom, may in particular be aromatic (i.e. an aryl group), or saturated or partially saturated. Preferred monocyclic carbocyclic groups of the invention include 5- and 6-membered monocyclic carbocyclic groups. Most preferred monocyclic carbocyclic groups of the invention include cyclohexyl and phenyl.

In the context of this invention a monocyclic heterocyclic group is a cyclic compound holding one or more heteroatoms in its ring structure. Preferred heteroatoms include nitrogen (N), oxygen (O), and sulphur (S). One or more of the ring structures may in particular be aromatic or partially saturated (i.e. a heteroaryl), or fully saturated. Preferred heterocyclic monocyclic groups of the invention include 5- and 6-membered heterocyclic monocyclic groups.

Preferred 5-6 membered monocyclic heterocyclic groups of the invention include furanyl, in particular furan-2- or 3-yl; thienyl, in particular thien-2- or 3-yl; selenophenyl, in particular selenophen-2- or 3-yl; pyrrolyl (azolyl), in particular pyrrol-2- or 3-yl; oxazolyl, in particular oxazol-2, 4- or 5-yl; thiazolyl, in particular thiazol-2, 4- or 5-yl; imidazolyl, in particular imidazol-2- or 4-yl; pyrazolyl, in particular pyrazol-3- or 4-yl; isoxazolyl, in particular isoxazol-3, 4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4- or 5-yl, or 1,3,4-thiadiazol-2-yl; pyridyl, in particular pyrid-2-, 3- or 4-yl; pyridazinyl, in particular pyridazin-3- or 4-yl; pyrimidinyl, in particular pyrimidin-2-, 4- or 5-yl; pyrazinyl, in particular pyrazin-2- or 3-yl; and triazinyl, in particular 1,2,4- or 1,3,5-triazinyl.

Most preferred 5-6 membered monocyclic heterocyclic groups of the invention include pyridinyl, in particular pyridin-2, 3 or 4-yl; pyridazinyl, in particular pyridazin-3- or 4-yl; pyrimidinyl, in particular pyrimidin-2, 4 or 5-yl; and pyrazinyl, in particular pyrazin-2 or 3-yl.

Pharmaceutically Acceptable Salts

The chemical compound for use according to the invention may be provided in any form suitable for the intended administration. Suitable forms include pharmaceutically (i.e. physiologically) acceptable salts, and pre- or prodrug forms of the chemical compound for use according to the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound for use according to the invention include, without limitation, the sodium, the potassium, the calcium, the magnesium, the lithium, and the ammonium salt, and the like, of a chemical compound of the invention containing an anionic group. Such cationic salts may be formed by procedures well known and described in the art.

Methods of Preparation

The compounds for use according to the invention may be prepared by conventional methods for chemical synthesis, e.g. those described in WO 94/22807, WO 96/25157, WO 97/45400, WO 97/45111, WO 98/47879, WO 2000/24707 and WO 2004/022529.

Pharmaceutical Compositions

In another aspect the invention provides novel pharmaceutical compositions comprising a therapeutically effective amount of a compound for use according to the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the compound for use according to the invention together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any person skilled in the art, by use of standard methods and conventional techniques, appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about I to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method of treatment, prevention or alleviation of a cardiac disease, disorder or condition of a living animal body, including a human, which disorder, disease or condition is responsive to activation of an ERG channel, in particular the human ERG1 channel (Human Ether-a-go-go Related Gene channel, HERG1 channel), which method comprises the step of administering to such a living animal body in need thereof, a therapeutically effective amount a compound capable of activating the ERG channel, or a pharmaceutically-acceptable addition salt thereof.

In a preferred embodiment the cardiac disease, disorder or condition is cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, or any other abnormal rhythm, e.g. caused by myocardial ischaemia, myocardial infarction, cardiac hypertrophy, cardiomyopathy or a genetic disease.

In another specific embodiment a cardiac disease, disorder or condition is cardiac ishemia, ishcemic heart disease, hypertrophic heart, cardiomyopathia or failing heart.

In a most preferred embodiment a cardiac disease, disorder or condition of the invention is cardiac arrhythmia.

It is at present contemplated that a suitable dosage of the active pharmaceutical ingredient (API) is within the range of from about 0.1 to about 1000 mg API per day, more preferred of from about 1 to about 500 mg API per day, most preferred of from about 1 to about 100 mg API per day, dependent, however, upon the exact mode of administration, the form in which it is administered, the indication considered, the subject and in particular the body weight of the subject involved, and further the preference and experience of the physician or veterinarian in charge.

BRIEF DESCRIPTION OF THE DRAWING

The present invention is further illustrated by reference to the accompanying drawing, in which.

EXAMPLES

The invention is further illustrated with reference to the following examples, which are not intended to be in any way limiting to the scope of the invention as claimed.

Example 1

Expression and Functional Characterization of the HERG1 Channel in Mammalian Cells In this example the HERG1 channel opening activity of a diphenyl urea derivative for use according to the invention, 1-(3-Trifluoromethyl-phenyl)-3-(2-hydroxy-5-chlorophenyl)-urea (Compound A), is determined using mammalian HEK293 cells stably expressing HERG1 channels.

Cloning and Expression

The HERG1 channel is expressed in HEK293 cells. The gene encoding the HERG1 channel was cloned as described by Warmke & Ganetzky; *Proc. Natl. Acad. Sci. USA* 1994 91 3438-3442.

To ensure functional expression in HEK293 cells, the HERG1 gene was sub-cloned in the shuttle-vector pXOOM as described by Jespersen et al.; *Biotechniques* 2002 32 536-540.

Mammalian expression is obtained by stable transfection of the gene construct in HEK293 cells.

Electrophysiological Determination

The electrical current through the HERG1 channel is measured using patch clamp technology. HERG1 current is activated by simulated cardiac action potentials.

In brief, this protocol goes from a resting membrane potential of −90 mV to a short initial depolarisation step to +30 mV, followed by a ramp ending at 0 mV. This plateau phase is ended by a repolarisation, going from −15 mV to −90 mV in 70 ms, back to the resting membrane potential, as also shown in the voltage protocol in FIG. 1.

Results

Figure 1:
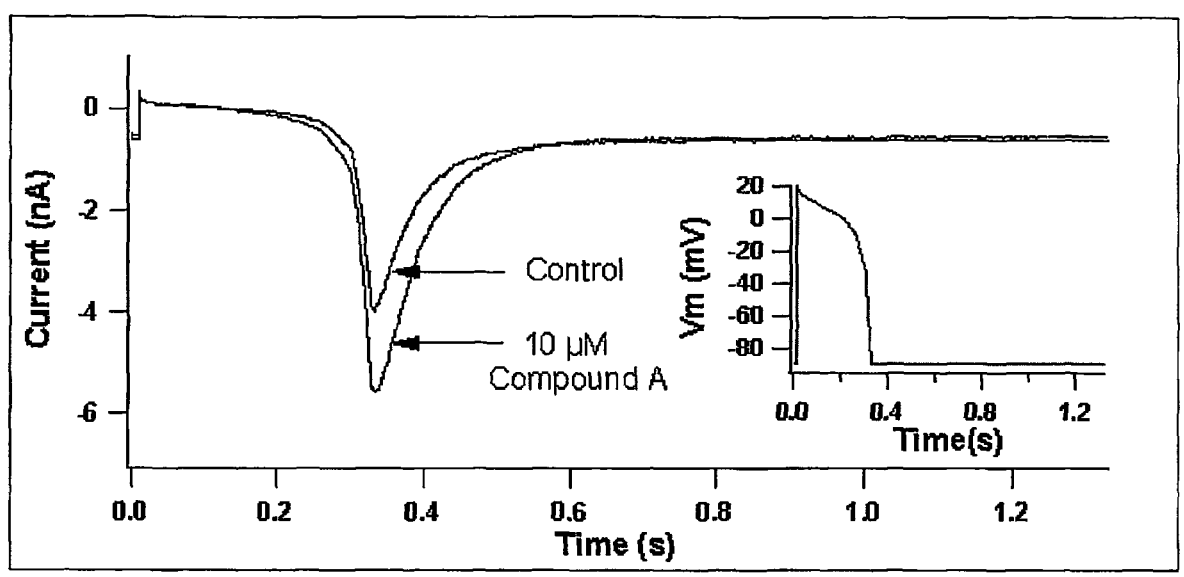
FIG. 1 shows a determination of the current (−6 to 0 nA) vs. time (0.0 to 1.2 seconds). Mammalian HEK293 cells stably expressing HERG 1 channels are challenged by a simulated cardiac action potential as indicated in the figure. Having reached a stable current level Compound A was added. Current traces are shown for a control experiment and in response to 10 µM of Compound A, A marked increase in the repolarisation current is observed.

HEK293 cells stably expressing HERG1 channels where challenged by a cardiac action potential protocol as indicated in FIG. 1. Having reached a stable current level, Compound A was added. A marked increase in the repolarisation current could be observed.

The results are presented in FIG. 1.

In experiments performed in HEK293 cells administration of 3-30 µM of Compound A resulted in an increase in the current during the last phase of the cardiac simulating voltage protocol reflecting the repolarisation current in a native cardiac action potential.

It was also noticed that the first 200 ms of the resting phase had an increased HERG1 current.

Example 2

Expression and Functional Characterization of the HERG1 Channel in *Xenopus laevis* oocytes In this example the HERG1 channel opening activity of a diphenyl urea derivative for use according to the invention, 1-(3-Trifluoromethyl-phenyl)-3-[2-(1H-tetrazol-5-yl)-4-bromo-phenyl] urea (Compound B), obtained as described in WO 98/47879, Example 1, and N-[3-(1H-Tetrazol-5-yl)-biphenyl-4-yl]-3,5-bis-trifluoromethyl-benzamide (Compound 15), obtained as described in Example 5, respectively, is determined using *Xenopus laevis* oocytes transiently expressing HERG1 channels.

Cloning and Expression

The HERG1 channel is expressed in HEK293 cells. The gene encoding the HERG1 channel was cloned as described by Warmke & Ganetzky, *Proc. Natl. Acad. Sci. USA* 1994 91 3438-3442.

To ensure functional expression in HEK293 cells, the HERG1 gene was sub-cloned in the shuttle-vector pXOOM as described by Jespersen et al.; *Biotechniques* 2002 32 536-540.

Electrophysiological Determination

The electrical current through the HERG1 channel is measured using 2-electrode voltage clamp technology. HERG1 current is activated by a step protocol.

In brief, this protocol goes from a resting membrane potential of −80 mV (lasting 3 seconds) to a 1 second depolarisation step at +10 mV, followed by a repolarisation step at −60 mV. The protocol is repeated up to 500 times.

Results

*Xenopus laevis* oocytes transiently expressing HERG1 channels where challenged by a voltage protocol from −80 mV to +10 mV to −60 mV. This protocol was repeated every $7^{th}$ second until a stable current level was obtained. In independent experiments either of Compound B and Compound 15 were added. A marked increase in the repolarisation current recorded at −60 mV could be observed.

Figure 2:
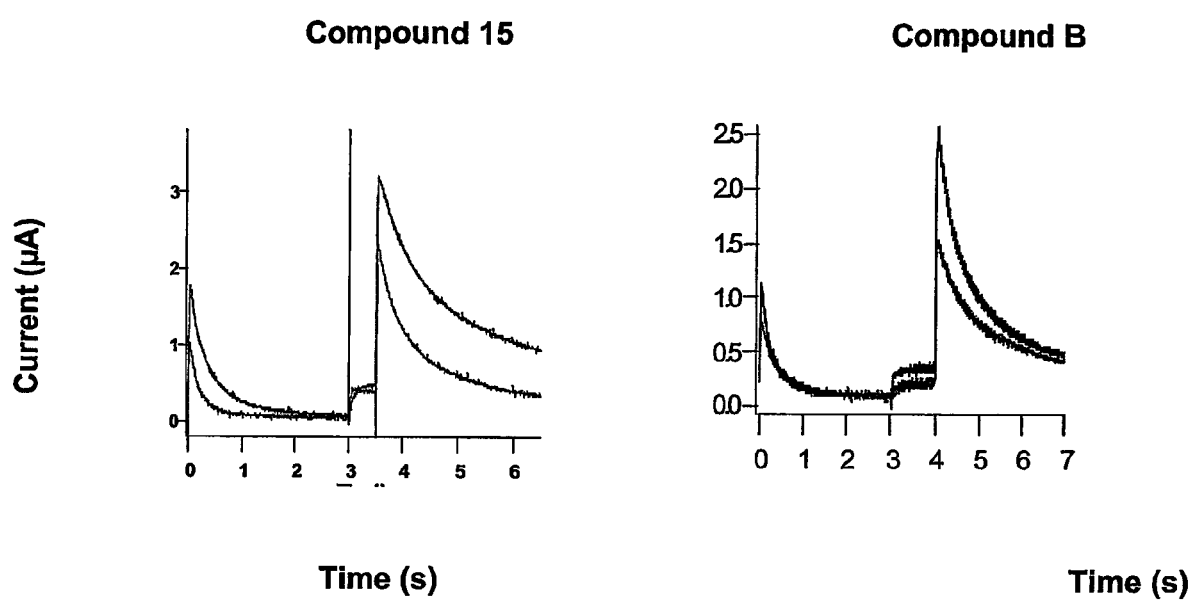
FIG. 2 shows results from *Xenopus laevis* oocytes transiently expressing HERG1 channels. Results are obtained by voltage clamping protocols stepping from 3 seconds at −80 mV to 1 second at +10 mV, followed by a step to 3 seconds at −60 mV. Current traces are shown for control experiments and in the response to 30 µM of either Compound B or Compound C. The tail current refers to the current measured at a potential of −60 mV.

The results are presented in FIG. 2.

In experiments performed in *Xenopus laevis* oocytes, administration of 1-30 µM of Compound B and Compound 15 resulted in an increase in the current.

Example 3

Modulation of Action Potentials in Native Cardiac Myocytes

In this example the activity on native cardiac myocytes from guinea pigs of a compound representative of the invention, 1,3-Bis-(2-hydroxy-5-trifluoromethyl-phenyl)-urea (Compound C), obtained as described in WO 2002/064128, is determined.

Electrophysiological Determination

The membrane potential of native cardiomyocytes was determined using the patch clamp technique in current clamp mode. The membrane potential was adjusted to approximately −80 mV before start of experiments. Cells were challenged by 20 repetitive rounds of current applications. A single round of application was as follows: Action potentials were evoked by applying a single current pulse of 1 nA lasting from 5-15 ms. The single pulse was followed by 30 repetitive pulses lasting 1-5 ms and with a current amplitude of 100-700 pA. The repetitive pulses were applied at the end of the evoked action potential. These experiments were conducted in the presence or absence of Compound C.

Results

Figure 3:
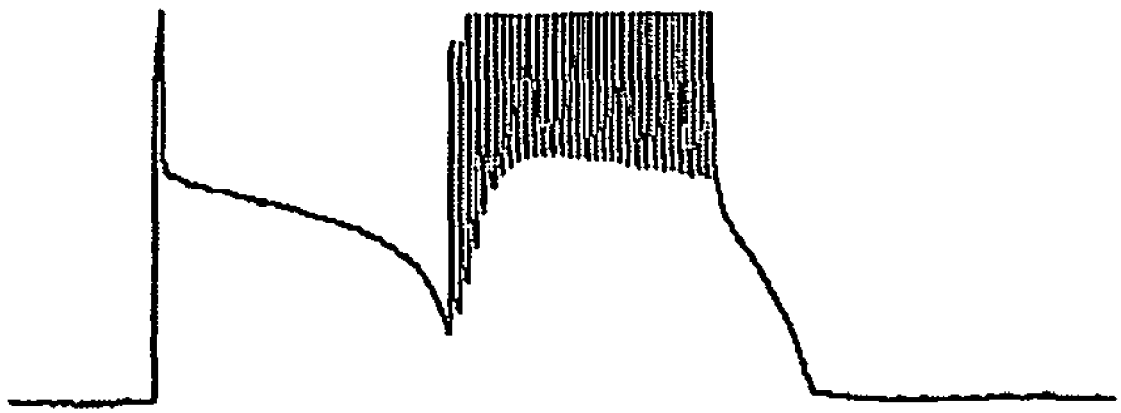
FIG. 3 shows results from guinea pig cardiomyocytes. Cardiac action potentials are initiated by injection of current. At a time point close to full repolarization, the cells are challenged by sub-threshold current injections to mimic delayed after-depolarizations. In control situations the summation of these current injections are sufficient to trigger a new action potential. In this experiment, however, application of 10-30 µM of Compound D stabilizes the cell and reduces the length of the cardiac action potential, thereby making it resistant to the later current injections. Results are obtained in current clamp mode and action potentials are evoked by current injection. Current traces are shown for control experiments and in the response to 30 µM of Compound D.
Figure 3:
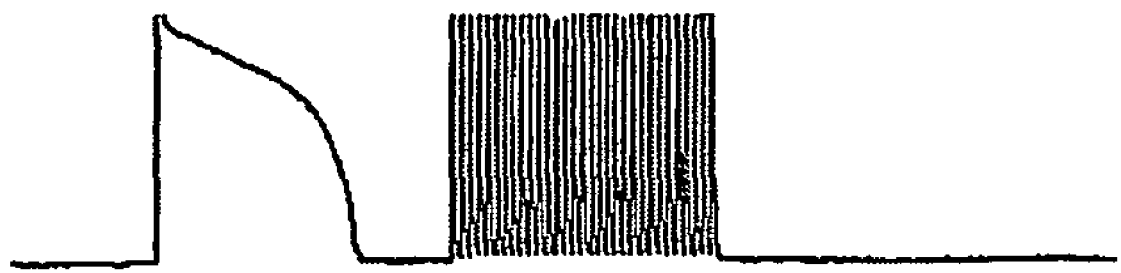

Native cardiomyocytes responded to the described voltage protocol by eliciting an actionpotential. The following repetitive pulses (simulating early or late after-depolarisations) resulted in disturbance of the cardio myocyte membran potential and thereby prevented a regular repolarisation of the membrane potential. This was observed in 10 out of 20 rounds of current applications in control experiments (a representative example of a disturbed membrane potential is demonstrated in FIG. 3). In contrast, application of Compound C resulted in a shorting of the cardiac action potential and a stable membrane potential in the presence of the 30 repetitive pulses as demonstrated in FIG. 3. This stabilisation was observed for all 20 rounds of current applications.

Example 4

Modulation of QT Intervals in Electrocardiograms of Guinea Pigs

In this experiment the compounds contemplated used according to the invention were investigated in an awake guinea-pig telemetry model typically used for safety evaluation with regard to human ERG-blockers.

Compounds were dosed IV, and ECG's and heart rate were measured. QT intervals were corrected (QTc) for any change in heart rate.

In this model, it is possible to obtain a dose-related decrease in QT intervals with compounds that open HERG channels, confirming that this channel is important for termination (repolarization) of the guinea pig cardiac action potential.

Figure 4:
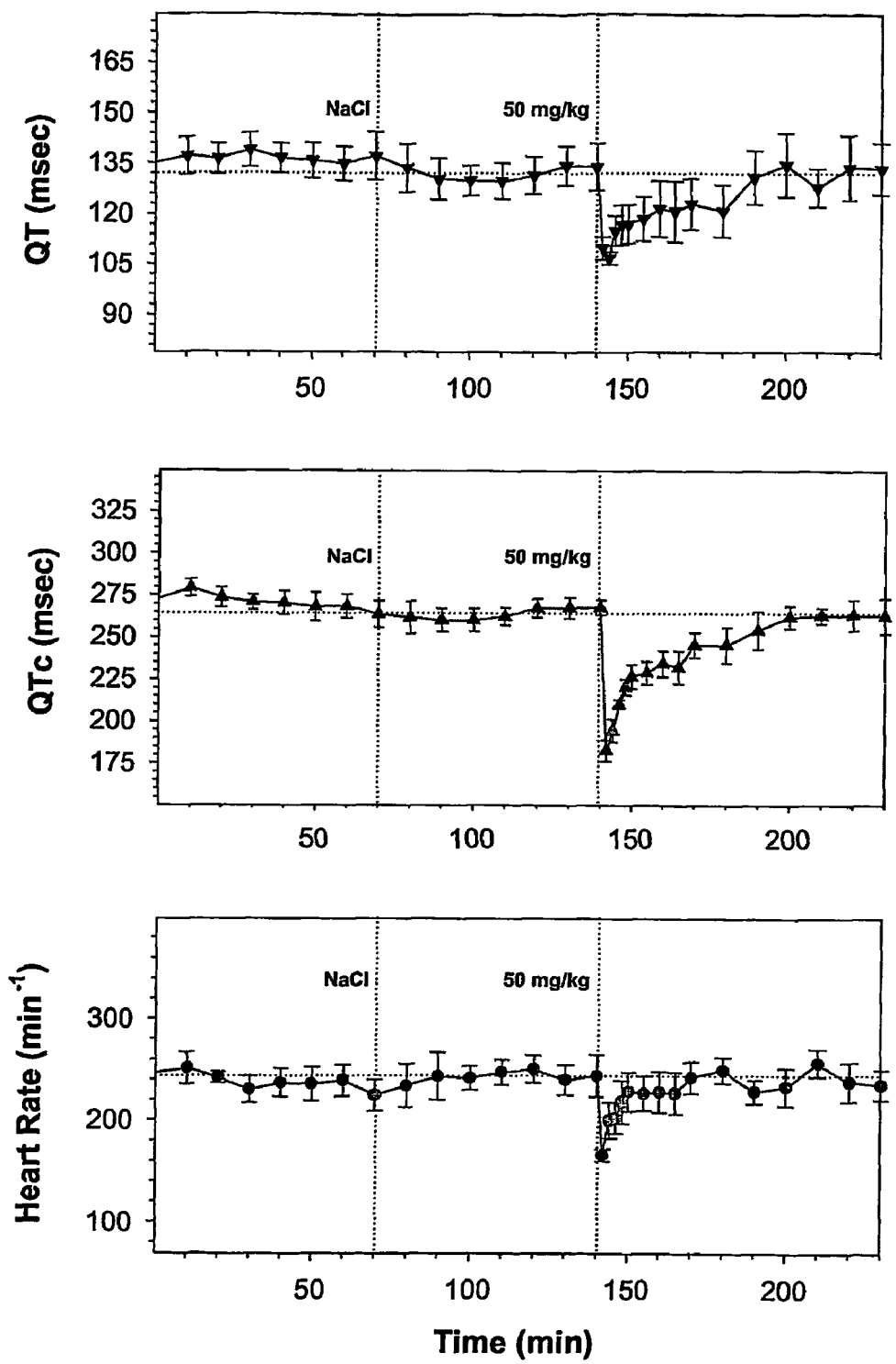
FIG. 4 shows the QT interval (QT; msec.), QT interval corrected for heart rate (QTc; msec.), and Heart Rate (per minute) over time (0-230 minutes) measured by telemetry in awake guinea pigs using a guinea-pig telemetry model, according to which model heart rate and ECG measurements are obtained before and after IV administration of 50 mg/kg of Compound B. IV application of Compound B has a dramatic effect on the corrected QT interval, reducing the length by 23% when compared to controls.

The results of this experiment are presented in FIG. 4 that demonstrates the effect of one concentration (50 mg/kg) of Compound B.

Example 5

Preparatory Example 1-(2-Hydroxy-5-trifluoromethyl-phenyl)-3-(2-trifluoromethyl-phenyl)-urea (Compound 1);

1-(2-Methoxy-5-trifluoromethyl-phenyl)-3-(2-trifluoromethyl-phenyl)-urea (1 g) was dissolved in dry dichloromethane (20 ml) and cooled in an ice-bath. A 1M solution of $BBr_3$ in dichloromethane (4 ml) was added drop-wise, and the solution stirred at room temperature for 30 minutes. Water was added, and after vigorous stirring, the mixture was extracted with dichloromethane. Drying ($MgSO_4$), filtration, concentration in vacuo and flash chromatography provided a product which was slurried with petrol, filtered, washed with petrol and dried to afford 1-(2-Hydroxy-5-trifluoromethyl-phenyl)-3-(2-trifluoromethyl-phenyl)-urea (340 mg). Mp.=158-159° C.

1-Pyrimidin-2-yl-3-(2-trifluoromethyl-phenyl)-urea (Compound 2):

2-Aminopyrimidine (1 g) was suspended in toluene (50 ml) and treated with 3-trifluoromethylphenylisocyanate (1.5 ml). The reaction was stirred overnight and then concentrated in vacuo to provide a white solid, which was taken up in 700 ml of boiling methanol and filtered. The filtrate was refluxed to provide a clear solution, which was slowly cooled to 3° C. overnight. Filtration, washing with methanol and air drying gave 1-Pyrimidin-2-yl-3-(2-trifluoromethyl-phenyl)-urea (2.24 g). Mp.=224-225° C.

1-(5-Chloro-2-hydroxy-phenyl)-3-(2-trifluoromethyl-phenyl)-urea (Compound 3):

5-Chloro-2-hydroxyaniline (1 g) was suspended in toluene (50 ml) and treated with 2-trifluoromethylphenylisocyanate (1.2 ml). The reaction was stirred overnight and then filtered. The filter-cake was slurried and filtered twice with 15 ml toluene and washed once more with petrol. Drying at 55° C. gave 1-(5-Chloro-2-hydroxy-phenyl)-3-(2-trifluoromethyl-phenyl)-urea (2.06 g). Mp.=183-184° C.

1-(2-Hydroxy-6-methoxy-pyridin-3-yl)-3-(3-trifluoromethyl-phenyl)-urea (Compound 4):

1-(2,6-dimethoxy-pyridin-3-yl)-3-(3-trifluoromethyl-phenyl)-urea (0.5 g) was suspended in dry dichloromethane (10 ml), $BBr_3$ (0.14 ml) was added and the solution stirred at room temperature. After 5 hours more $BBr_3$ (50 μl) was added and after a further hour the reaction was diluted with more dichloromethane and quenched with ice-water. The mixture was extracted with ethyl acetate, dried over $MgSO_4$, filtered and concentrated to provide a light purple residue. This was preloaded onto silica and chromatographed to provide 1-(2-Hydroxy-6-methoxy-pyridin-3-yl)-3-(3-trifluoromethyl-phenyl)-urea as a white solid (210 mg). Mp.=223-224° C.

1-(1-Oxy-pyridin-2-yl)-3-(3-trifluoromethyl-phenyl)-urea (Compound 5):

1-(Pyridin-2-yl)-3-(3-trifluoromethyl-phenyl)-urea (1 g) in dichloromethane (50 ml) was treated with 60% m-CPBA (1 g) and stirred at room temperature overnight. The mixture was concentrated, taken up in EtOAc (60 ml), warmed and cooled to room temperature. Filtration and washing with EtOAc and drying in air gave 1-(1-Oxy-pyridin-2-yl)-3-(3-trifluoromethyl-phenyl)-urea as a white solid (820 mg). Mp.=213-214° C. 1-(3,5-Dihydroxyphenyl)-3-(3-trifluoromethyl-phenyl)-urea (Compound 6):

1-(3,5-dimethoxyphenyl)-3-(3-trifluoromethyl-phenyl)-urea (1 g) in dichloromethane (25 ml) was treated with $BBr_3$ (1 ml) and stirred at room temperature for 3 hours before pouring into water and filtration. The oily residue was chromatographed on silica to provide, along with some mono-demethylated product, the 1-(3,5-Dihydroxyphenyl)-3-(3-trifluoromethyl-phenyl)-urea (130 mg). Mp.=174-175° C.

2,6-Dioxo-5-[3-(3-trifluoromethyl-phenyl)-ureido]-1,2,3,6-tetrahydro-pyrimidine-4-carboxylic acid (Compound 7):

5-Amino-orotic acid (0.86 g) was dissolved in DMSO (10 ml), treated with 3-trifluoromethylphenylisocyanate (0.9 ml) and after an hour with another 0.5 ml. The reaction was stirred for three days at room temperature. Water was added and the mixture was filtered and washed with water. The residue was slurried in water, treated with NaOH and worked through until basic. Filtration and acidification of the filtrate provided a precipitate, which was filtered, washed with water and dried. Recrystallisation from 96% EtOH provided 2,6-dioxo-5-[3-(3-trifluoromethyl-phenyl)-ureido]-1,2,3,6-tetrahydro-pyrimidine-4-carboxylic acid (330 mg). Mp. >300° C.

3-[3-(3-Trifluoromethyl-phenyl)-ureido]-pyrazine-2-carboxylic acid (Compound 8);

3-Aminopyrazine-2-carboxylic acid (0.7 g) in DMSO (10 ml) was treated with 3-trifluoromethylphenylisocyanate (0.9 ml), stirred at room temperature overnight and then quenched with water. A gummy residue separated. After decantation the residue was washed thoroughly with water, stirred with NaOH to basic pH, filtered and chromatographied on silica with $CH_2Cl_2$:MeOH:acetone (4:1:1) followed by $CH_2Cl_2$:MeOH:$NH_4OH$ (40:9:1) when the product started coming off the column. This gave 3-[3-(3-trifluoromethyl-phenyl)-ureido]-pyrazine-2-carboxylic acid. Mp.>300° C.

4-Chloro-2-[3-(2-fluoro-phenyl)-ureido]-benzoic acid (Compound 9):

2-Amino-4-chlorobenzoic acid (0.3 g), 2-fluorophenylisocyanate (0.2 ml) and triethylamine (0.24 ml) were stirred in toluene (20 ml) for a week. More 2-fluorophenylisocyanate (0.1 ml) was added and stirring continued for another week.

The mixture was concentrated to almost dry, water was added and the pH was adjusted to 1 with diluted HCl. Water was decanted and the residue was dissolved in warm 96% EtOH. The pH was adjusted to 1 again with 4N HCl resulting in the precipitation of a solid, which was filtered and dried to give 4-chloro-2-[3-(2-fluoro-phenyl)-ureido]-benzoic acid (0.25 mg). Mp.=195-197° C.

4-Chloro-2-[3-(3-trifluromethyl-phenyl)-ureido]-benzene-sulfonamide (Compound 10):

This compound was prepared in a manner analogous to 1-Pyrimidin-2-yl-3-(2-trifluoromethyl-phenyl)-urea (Compound 2) from 2-amino-4-chloro-benzenesulfonamide and 3-trifluoromethylphenylisocyanate, yielding 4-chloro-2-[3-(3-trifluromethyl-phenyl)-ureido]-benzenesulfonamide (550 mg). Mp.=163-165° C.

3-[4-[3-(4-Chloro-3-trifluoromethyl-phenyl)-ureido]-3-(1H-tetrazol-5-yl)-phenyl]-N,N-dimethyl-propionamide (Compound 11);

3-[4-Amino-3-(1H-tetrazol-5-yl)-phenyl]-N,N-dimethyl-propionamide (90 mg) dissolved in acetonitrile at 65° C. under Ar was treated with 4-chloro-3-trifluoromethylphenylisocyanate (85.6 mg) and the mixture was stirred overnight. Cooling to room temperature and filtration afforded 3-[4-[3-(4-chloro-3-trifluoromethyl-phenyl)-ureido]-3-(1H-tetrazol-5-yl)-phenyl]-N,N-dimethyl-propionamide. Mp.=184.5-189.3° C.

1-[4-Chloro-2-(1H-tetrazol-5-yl)-phenyl]-3-(3,5-dichloro-phenyl)-urea (Compound 12):

4-Chloro-2-(1H-tetrazol-5-yl)-phenylamine (500 mg) dissolved in toluene (15 ml) was treated with 3,5-dichlorophenylisocyanate (500 mg) and stirred for a week. The precipitated product was filtered, washed with toluene, dissolved in acetone, filtered through celite, precipitated again with water, filtered and dried. This residue was slurried in 96% EtOH, and adjusted to basic pH with 10 N NaOH. The solution was filtered through celite and re-acidified with 4N HCl and a little water. The precipitated product was filtered and washed with water to afford 1-[4-Chloro-2-(1H-tetrazol-5-yl)-phenyl]-3-(3,5-dichloro-phenyl)-urea as a white solid (720 mg). Mp.=234-236° C.

1-[4-Chloro-2-(1H-tetrazol-5-yl)-phenyl]-3-(4-chloro-3-trifluoromethyl-phenyl)-urea (Compound 13):

4-Chloro-2-(1H-tetrazol-5-yl)-phenylamine (500 mg) dissolved in toluene (15 ml) was treated with 4-chloro-3-trifluoromethylphenylisocyanate (600 mg) and stirred for a week. The precipitated product was filtered and then acid/base extracted and re-precipitated in aq. acid in a manner analogous to that described for 1-[4-Chloro-2-(1H-tetrazol-5-yl)-phenyl]-3-(3,5-dichloro-phenyl)-urea (Compound 12) to give 1-[4-Chloro-2-(IH-tetrazol-5-yl)-phenyl]-3-(4-chloro-3-trifluoromethyl-phenyl)-urea as a white solid (850 mg). Mp.=245-247° C.

3'-(5-Oxo-4,5-dihydro-[1,2,4]oxadiazol-3-yl)4'-[3-(3-trifluromethyl-phenyl)-ureido]-biphenyl-4-carboxylic acid dimethylamide (Compound 14):

3'-(N-lsobutoxycarbonyloxycarbamimidoyl)-4'-[3-(3-trifluoromethyl-phenyl)-ureido]-biphenyl-4-carboxylic acid dimethylamide (150 mg) in dioxan (6 ml) was adjusted to pH >10 with 1N NaOH and stirred at room temperature for 2.5 hrs. Addition of water, extraction with EtOAc, washing with brine, drying ($Na_2SO_4$), filtration and concentration afforded 3'-(5-Oxo-4,5-dihydro-[1,2,4]oxadiazol-3-yl)-4'-[3-(3-trifluromethyl-phenyl)-ureido]-biphenyl-4-carboxylic acid dimethylamide as a light yellow solid (102 mg). Mp.>165° C. (dec.).

N-[3-(1H-Tetrazol-5-yl)-biphenyl-4-yl]-3,5-bis-trifluoromethyl-benzamide (Compound 15):

N-[3-cyano-biphenyl-4-yl]-3,5-bis-trifluoromethyl-benzamide (100 mg), sodium azide (40 mg) and triethylamine hydrochloride (103 mg) were stirred at 100° C. for 20 hours in DMF (3 ml). The reaction mixture was poured into a 5% $KHSO_4$ solution (10 ml) and the solid was filtered off and dried to give N-[3-(1H-Tetrazol-5-yl)-biphenyl-4-yl]-3,5-bis-trifluoromethyl-benzamide as a white solid (120 mg). Mp.=156° C. (dec.).

3'-(5-Oxo-4,5-dihydro-1H-1,2,4ltriazol-3-yl)-4'-[3-(3-trifluromethyl-phenyl)-ureido]-biphenyl-4-carboxylic acid dimethylamide (Compound 16):

A solution of 3'-(N-aminocarbamimidoyl)-4'-[3-(3-trifluoromethyl-phenyl)-ureido]-biphenyl-4-carboxylic acid dimethylamide (322 mg) and triethylamine (212 microliters) dissolved in dichloromethane (5 ml) at -50° C. was treated with a solution of triphosgene (236 mg) in dichloromethane (5 ml). The mixture was stirred for 2.5 hrs at ambient temperature and poured into water. After adjusting to pH 7 with aq. sodium bicarbonate, the mixture was extracted with EtOAc. The organic layers were dried over $Na_2SO_4$, filtered and concentrated. Column chromatography on silica afforded 3'-(5-Oxo-4,5-dihydro-1H-[1,2,4]triazol-3-yl)-4'-[3-(3-trifluromethyl-phenyl)-ureido]-biphenyl-4-carboxylic acid dimethylamide as a white solid. Mp.=212° C.

N-[3-Chloro-4-(4-chloro-phenylamino)-phenyl]-2-hydroxy-5-nitro-benzamide (Compound 17):

N-[3-Chloro-4-(4-chloro-phenylamino)-phenyl]-2-acetoxy-5-nitro-benzamide (155 mg) was dissolved in a 1:1 mixture of THF and water (12 ml) and $LiOH.H_2O$ (64 mg) was added. After stirring at room temperature for 2 hours the solvents were evaporated and water was added to the residue. Filtration, acidification of the filtrate and filtration of the precipitate gave a residue which was flash-chromatographed (EtOAc; 1:3) to provide N-[3-Chloro-4-(4-chloro-phenylamino)-phenyl]-2-hydroxy-5-nitro-benzamide as a curry coloured powder (70 mg). Mp. >219° C. (dec.).

The invention claimed is:

1. A method of treatment or alleviation of an abnormal rhythm of the heart of a living animal body, which method comprises the step of administering to such a living animal body in need thereof, a therapeutically effective amount a compound capable of activating an ERG channel, or a pharmaceutically-acceptable addition salt thereof, wherein the compound capable of activating an ERG channel is 1,3-bis-(2-hydroxy-5-trifluoromethyl-phenyl)-urea

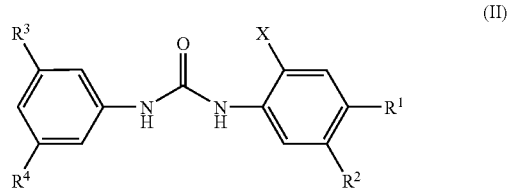

(II)

or an enantiomer thereof or a mixture of its enantiomers.

2. The method according to claim 1, wherein the abnormal rhythm of the heart is cardiac arrhythmia, atrial arrhythmia, ventricular arrhythmia, atrial fibrillation, ventricular fibrillation, tachyarrhythmia, atrial tachyarrhythmia, ventricular tachyarrhythmia, or bradyarrhythmia.

3. The method according to claim 1, wherein the abnormal rhythm of the heart is cardiac ishemia, ishcemic heart disease, hypertrophic heart, cardiomyopathia or failing heart.

4. The method according to claim 1, wherein the abnormal rhythm of the heart is cardiac arrhythmia, atrial fibrillation and/or ventricular tachyarrhythmia.

5. The method according to claim 1, wherein the abnormal rhythm of the heart is cardiac arrhythmia.

6. The method of treatment or alleviation of an abnormal rhythm of the heart of a living animal body according to claim 1, wherein said living animal body is a human body.

* * * * *